(12) United States Patent
Butterfield et al.

(10) Patent No.: US 8,979,897 B2
(45) Date of Patent: Mar. 17, 2015

(54) INTERSPINOUS IMPLANT

(75) Inventors: Forbes Butterfield, Glasgow (GB); Paul Trickett, Hamilton (GB)

(73) Assignee: QSpine Limited, Kettering (GB)

( * ) Notice: Subject to any disclaimer, the term of this patent is extended or adjusted under 35 U.S.C. 154(b) by 165 days.

(21) Appl. No.: 13/518,242

(22) PCT Filed: Dec. 22, 2010

(86) PCT No.: PCT/GB2010/002333
§ 371 (c)(1),
(2), (4) Date: Aug. 30, 2012

(87) PCT Pub. No.: WO2011/077101
PCT Pub. Date: Jun. 30, 2011

(65) Prior Publication Data
US 2013/0012995 A1    Jan. 10, 2013

(30) Foreign Application Priority Data
Dec. 23, 2009  (GB) .................................. 0922614.3

(51) Int. Cl.
*A61B 17/70*  (2006.01)
*A61B 17/88*  (2006.01)

(52) U.S. Cl.
CPC ......... *A61B 17/7053* (2013.01); *A61B 17/7062* (2013.01); *A61B 17/8869* (2013.01); *A61B 17/8861* (2013.01)
USPC .......................... 606/249; 606/86 A; 606/279

(58) Field of Classification Search
CPC ........... A61B 17/7053; A61B 17/8861; A61B 17/8869; A61B 17/7062–17/7071
USPC .............................. 606/246, 248–249; 24/193
See application file for complete search history.

(56) References Cited

U.S. PATENT DOCUMENTS 2,246,170 A * 6/1941 Gise ................................ 24/193
2,290,234 A * 7/1942 Gilmore .......................... 24/193
(Continued)

FOREIGN PATENT DOCUMENTS

EP           1367954        12/2003
KR      10-2007-0068986      7/2007
(Continued)

OTHER PUBLICATIONS

"Mechanical Supplementation by Non-Rigid Fixation in Degenerative Intervertebral Lumbar Segments: The Wallis System", J. Senegas, Eur Spine J (2002) 11 (Suppl. 2): S164-S169.
(Continued)

*Primary Examiner* — Eduardo C Robert
*Assistant Examiner* — Jacqueline Johanas
(74) *Attorney, Agent, or Firm* — Marshall, Gerstein & Borun LLP

(57) ABSTRACT

An interspinous implant includes an implant body having an upper face, a lower face, and four sides. The implant body includes a first recess and a second recess in opposite sides, wherein each recess is suitable for receiving a spinous process of a vertebrae. Attachment means are provided and suitable for attaching a band to the implant body. The implant further includes a lock hinged to a side of the implant body on a side not having the recesses, with the lock rotatable about the hinge between a closed position and an open position in which the lock projects away from the side of the implant body. The lock has an aperture, and a band can pass through the aperture when the lock is open and can be secured against movement relative to the lock and the implant body by the lock when the lock is closed.

12 Claims, 3 Drawing Sheets

(56) References Cited

U.S. PATENT DOCUMENTS

| | | | |
|---|---|---|---|
| 3,641,630 A * | 2/1972 | Farley | 24/68 CD |
| 4,001,920 A * | 1/1977 | Johnson | 24/193 |
| 4,751,772 A * | 6/1988 | Crowle | 24/170 |
| 4,815,175 A * | 3/1989 | Kasai | 24/193 |
| 5,437,685 A * | 8/1995 | Blasnik | 606/151 |
| 5,496,318 A * | 3/1996 | Howland et al. | 606/249 |
| 6,605,091 B1 * | 8/2003 | Iwanski | 606/74 |
| 6,626,944 B1 | 9/2003 | Taylor | |
| 6,695,852 B2 * | 2/2004 | Gleason | 606/103 |
| 6,761,720 B1 * | 7/2004 | Senegas | 606/249 |
| 6,946,000 B2 * | 9/2005 | Senegas et al. | 623/17.11 |
| 7,087,083 B2 * | 8/2006 | Pasquet et al. | 623/17.11 |
| 7,163,558 B2 * | 1/2007 | Senegas et al. | 623/17.11 |
| 7,588,601 B2 * | 9/2009 | Le Couedic et al. | 623/17.16 |
| 7,635,377 B2 * | 12/2009 | Zucherman et al. | 606/249 |
| 7,909,853 B2 * | 3/2011 | Zucherman et al. | 606/249 |
| 8,002,805 B2 * | 8/2011 | Le Couedic et al. | 606/263 |
| 8,012,209 B2 * | 9/2011 | Zucherman et al. | 623/17.11 |
| 8,096,998 B2 * | 1/2012 | Cresina | 606/103 |
| 8,187,305 B2 * | 5/2012 | Malandain et al. | 606/248 |
| 8,187,306 B2 * | 5/2012 | Fallin et al. | 606/249 |
| 8,388,657 B2 * | 3/2013 | Boyer et al. | 606/249 |
| 8,696,710 B2 * | 4/2014 | Fielding et al. | 606/263 |
| 2002/0067036 A1 * | 6/2002 | Young et al. | 280/819 |
| 2002/0099377 A1 | 7/2002 | Zucherman et al. | |
| 2003/0083669 A1 * | 5/2003 | Gleason | 606/103 |
| 2004/0117017 A1 | 6/2004 | Pasquet et al. | |
| 2005/0075634 A1 * | 4/2005 | Zucherman et al. | 606/61 |
| 2005/0192581 A1 * | 9/2005 | Molz et al. | 606/74 |
| 2005/0209603 A1 * | 9/2005 | Zucherman et al. | 606/90 |
| 2006/0064165 A1 | 3/2006 | Zucherman et al. | |
| 2006/0085069 A1 * | 4/2006 | Kim | 623/17.11 |
| 2006/0235532 A1 * | 10/2006 | Meunier et al. | 623/17.16 |
| 2007/0093825 A1 | 4/2007 | Ferree et al. | |
| 2007/0203491 A1 * | 8/2007 | Pasquet et al. | 606/61 |
| 2008/0033556 A1 * | 2/2008 | Le Couedic et al. | 623/17.16 |
| 2008/0033557 A1 * | 2/2008 | Pasquet et al. | 623/17.16 |
| 2008/0082172 A1 * | 4/2008 | Jackson | 623/17.16 |
| 2008/0114357 A1 * | 5/2008 | Allard et al. | 606/61 |
| 2008/0177298 A1 | 7/2008 | Zucherman et al. | |
| 2008/0234747 A1 * | 9/2008 | Allard et al. | 606/279 |
| 2009/0138045 A1 * | 5/2009 | Ciupik et al. | 606/249 |
| 2010/0023056 A1 * | 1/2010 | Johansson et al. | 606/232 |
| 2010/0023060 A1 * | 1/2010 | Bennett et al. | 606/263 |
| 2010/0179595 A1 | 7/2010 | Jackson et al. | |
| 2010/0256680 A1 * | 10/2010 | Pasquet et al. | 606/249 |

FOREIGN PATENT DOCUMENTS

| | | |
|---|---|---|
| WO | WO-02/071960 | 9/2002 |
| WO | WO-2007/035120 | 3/2007 |
| WO | WO-2009/149414 | 12/2009 |

OTHER PUBLICATIONS

International Search Report in PCT/GB2010/002333 dated May 19, 2011.

* cited by examiner

INTERSPINOUS IMPLANT

FIELD OF THE INVENTION

The present invention relates to an interspinous implant, a method of making an interspinous implant, and methods of using an interspinous implant. The interspinous implant of the present invention is useful for stabilising the spine and providing disc support for patients suffering from various conditions known generally as degenerative disc disease. The present invention also relates to a tightening system that is suitable for use with an interspinous implant. This leads to improvements in the method of installation of the interspinous implant.

BACKGROUND TO THE INVENTION

Interspinous implants comprising an implant body designed to be inserted between the spinous processes of adjacent vertebrae and limit their movement with respect to one another are well known. While the implants are designed to restrict the relative movement of the adjacent vertebrae, they do not prevent movement all together, so are a good alternative to fusion for many conditions. Such implants have been successfully used for a number of years to stabilise the spine and provide disc support for patients suffering from various conditions known generally as degenerative disc disease. These implants represent a very useful tool in spinal surgery, especially since the procedure is reversible and leaves other options open in the future.

U.S. Pat. No. 6,626,944 discloses a basic version of one such implant, which has a implant body with recesses that define an interspinous portion designed to contact spinous processes of adjacent vertebrae. The implant has a band that is attached on one side of the implant body and, in use, is fed around each spinous process then secured back to the implant body, thereby effectively tying the spinous processes to the implant to restrict relative movement.

Installing this type of implant necessitates a surgical procedure during which the interspinous ligament connecting the two spinous processes between which the implant is to be inserted is extracted and openings for inserting bands are formed in the superior and inferior interspinous ligaments. Before the implant is inserted, one end of the band is attached to the implant body. Once the implant body is in place, the other end of the band is fed around one of the spinous processes. When a single band is used to secure the implant body, the band is then fed around the adjacent spinous process and attached back to the implant body. A similar process can be used with two bands.

Although installing the implant body between the two spinous processes is relatively quick and easy, attaching the band to the implant body to secure the implant in place is much more challenging. This is mainly because the incision and muscle retraction provides only a very restricted area in which to work. This part of the procedure can be time consuming and complicated.

In U.S. Pat. No. 6,626,944 the band is secured to the implant body by passing the band through a conduit in the implant body, passing a sleeve over the band and crimping the sleeve to the band to prevent the band passing back through the conduit. Alternatively, the band can be secured by passing it through the conduit and then tying the band in a knot around the conduit. However, in practice crimping or tying knots in such a restricted space is very difficult and fiddly for the surgeon. In addition, the crimps or knots could work loose over time, which would mean that the implant is no longer secured to the spinous processes. If this happened, the implant would be ineffective, with the consequential negative effects on the patient.

A similar implant is described in EP 1367954 which aims to address some of these problems by providing "removable fixing members" separate from the implant body. These are designed to be attached to each side of the implant body, once this has been located in place between the adjacent spinous processes during a surgical procedure. Once the implant body is in place, a band is passed around each of the spinous processes. The end of each band is then passed though an aperture in the removable fixing member, the removable fixing member is rotated about 360° anti-clockwise relative to the implant body to ensure the band passes twice between the member and the implant body, and the fixing member is attached to the body of the implant in situ using abutments on the fixing member which snap into correspondingly shaped housing in the implant body. The band is then tightened to secure the implant in place.

The implant described in EP 1367954 has been marketed as the "Wallis® Implant". It has been used in practice and has been successful in treating and preventing various different conditions. See, for example, "Mechanical supplementation by non-rigid fixation in degenerative interspinous lumbar segments: the Wallis system" by J Senegas, Eur Spine J (2002) 11 (Suppl. 2):S164-S169.

However, the removable fixing members in EP 1367954 are, in practice, still extremely fiddly to use. It is particularly difficult to attach the removable fixing members to the implant body as this requires the application of lateral force to push the abutments of the removable fixing members so that they snap into the implant body housing, where lateral force is difficult to apply due to the space restrictions.

In addition, the surgeon must ensure that the band is passed in the correct direction through the removable fixing member, and that the removable fixing member is rotated 360° anti-clockwise relative to the implant body before attachment. This has proved to be counterintuitive and adds a significant degree of room for human error by the surgeon.

Once the removable fixing members of EP 1367954 have been attached to the body of the implant, the band must be tightened. However, if the band is pulled away from the implant body, or if the band is over-tightened, this has the effect of pulling the removable fixing member away from the implant body and can actually cause it to become detached from the implant body. Since tightening is the last stage of fitting the implant the surgeon may not notice, and accordingly the implant might be left in the patient with the removable fixing member not properly attached to the implant body. This means that the implant is not properly secured in place so will be less effective and may fail.

The present invention aims to address some of the problems encountered with current interspinous implants. In particular the present invention aims to provide an interspinous implant that is simpler and easier to fit, that reduces the possibilities for human error, and that provides a better and safer way of securing the implant in place.

As noted above, once the bands are in place around the spinous processes and have been attached to the implant body they must be tightened. Further problems with existing implant installation concerns the method of tightening. It is fiddly and difficult to manually pull the band to tighten it or to use a surgical instrument that has not been designed for this purpose, such as a pincers or pliers.

In prior art systems it is known to provide a tightening system which comprises a holder and a rod. The holder fits at its distal end onto an insert which in turn fits into cavities in the upper face of the interspinous implant. In this way the holder can be fitted to the implant. The holder has at its proximal end a handle with apertures through which the rod can pass. The rod has an aperture at its distal end. In use the holder is fitted to the implant and the rod is passed through the aperture in the holder and down to the level of the implant. The band is passed through the aperture in the rod and the rod is rotated relative to the holder to tighten the band. This represents an improvement over using manual tightening or non-specific tools but it still difficult to use. One reason for this is that it is difficult to ensure the rod is in the right place to contact the band and to pull it in a direction in which it can be tightened. Another reason is that the rotational force applied during tightening can easily be transferred to the whole implant rather than just the band, so can cause the implant to rotate in the implant body away from the position in which the surgeon installed it. In addition, as noted above, a removable fixing member can become detached from the implant body during tightening.

Accordingly, the present invention also aims to address some of the problems encountered in the tightening step of installing interspinous implants. In particular, the present invention aims to provide a tightening system that improves the ease of implant installation thus making it more reliable, reproducible and safer.

SUMMARY OF THE INVENTION

A first aspect of the invention provides an interspinous implant comprising:
  (i) a implant body which has an upper face, a lower face, and four sides, wherein the implant body comprises;
  a first recess in one side of the implant body, and a second recess in the opposing side of the implant body to the first recess, wherein each recess is suitable for receiving a spinous process of a vertebrae; and
  attachment means, which is suitable for attaching a band to the implant body; characterised in that the implant also comprises
  (ii) a lock which is hinged to a side of the implant body that does not have the first or second recess;
  wherein the lock can rotate about the hinge between a closed position in which the lock lies substantially within a cavity in the side of the implant body or against the side of the implant body and an open position in which the lock projects away from the side of the implant body;
  wherein the lock has an aperture, so that a band can be passed through the aperture in the lock when the lock is in the open position and the band can be secured against movement relative to the lock and the implant body by the lock when the lock is in the closed position.

A second aspect of the invention provides a method of making an interspinous implant according to any preceding claim, the method comprising the steps of:
  making the implant body;
  making the lock of the implant; and
  hinging the lock to the side of the implant body, so that it can rotate between a closed position in which the lock lies substantially within a cavity in the side of the implant body or against the side of the implant body, and an open position in which the lock projects away from the implant body.

A third aspect of the invention provides a method of fitting and implant in a subject, the method comprising the steps of:
  providing an interspinous implant according to the first aspect of the invention which has a band attached to it;
  inserting the implant body of the interspinous implant between the spinous processes of adjacent vertebrae so that the spinous processes are located in the recesses of the implant body;
  passing the free end of the band around a spinous process and through the aperture in the lock when the lock is in an open position; and
  closing the lock and tightening the band to secure the implant in place relative to the spinous processes.

A fourth aspect of the invention relates to the use of an implant according to the first aspect of the invention to treat degenerative disc disease or the symptoms caused by degenerative disc disease.

A fifth aspect of the invention relates to an implant substantially as shown in the attached Figures.

A sixth aspect of the invention relates to a tightening system which is suitable for use with an interspinous implant, the tightening system comprising:
  (i) a holder with engagement means at its distal end which is suitable for engagement with a cavity in an upper face of an interspinous implant;
  (ii) a tightening guide which can be placed over the holder wherein the tightening guide has at its distal end a plate which is suitable for engagement with the implant body of an interspinous implant to prevent relative rotational movement between the tightening guide and the implant body, wherein the plate provides an arcuate tightening surface, and wherein the tightening guide has at its proximal end a handle which had at least one aperture through it; and
  (iii) a tightening rod, wherein the tightening rod has at its distal end an aperture extending lengthwise through which a band can pass, and the tightening rod has at its proximal end a handle, wherein the tightening rod can be placed though the aperture in the handle of the tightening guide and extends to contact the arcuate tightening surface of the plate of the tightening guide, so that when a band is passed through the aperture of the tightening rod, the band can be tightened by rotating the tightening rod relative to the tightening guide.

A seventh aspect of the invention relates to a kit comprising an interspinous implant according to the first aspect of the invention and a tightening system according to the sixth aspect of the invention.

The interspinous implant of the present invention advantageously comprises a lock which is hinged to the implant body and is therefore provided as an integral part of the implant. Having an implant that comprises integral parts and so does not need to be assembled when it is in situ in the patient is a huge advantage over implants that do need to be assembled in situ as attaching parts when the implant is in situ is very fiddly, due to the restricted space available in the operating space.

The lock of the present invention can rotate about the hinge between a closed position and an open position. This allows a band to be passed through an aperture in the lock when the lock is in the open position and secured against movement relative to the lock and the implant body when the lock is in the closed position. In this way the implant can be safely and easily secured in place.

Since the lock is hinged to the implant body it has only a limited scope of movement relative to the implant body, between an open and a closed position. Therefore, there is no chance that the surgeon can wrongly orientate the lock and the scope for human error is greatly reduced compared to previous methods of attaching a band to the implant body of an interspinous implant. In addition, as the lock is securely attached to the implant body by the hinge, the lock cannot become detached from the implant body at any point during the procedure, including during tightening, which represents a significant advantageous safety feature.

The interspinous implant comprises an implant body which has an upper face, a lower face, and four sides. The outline of the upper and lower faces is generally approximately rectangular, and the outline of the overall shape of the implant is generally approximately cuboidal, but there are recesses extending on two sides through the width of the implant body and the other two sides generally have cavities in them, as explained below. By the four "sides" of the implant body we mean the regions that join corresponding edges of the upper and lower faces.

The implant body has a first recess in one side of the implant body, and a second recess in the opposing side of the implant body to the first recess, wherein each recess is suitable for receiving a spinous process of a vertebrae. By this we mean that the recesses have suitable dimensions to fit snugly around spinous processes of vertebrae of the human (or animal) body, as is the case with existing interspinous implants. In use the two recesses receive a spinous process each, from adjacent vertebrae. The recesses are normally in the shape of grooves, and extend through the whole width of the implant body, so that when viewing the implant body from above (i.e. the upper surface) the implant body has a roughly "H" shaped profile, with the recesses forming the deviations from the overall approximately rectangular outline.

The implant body comprises attachment means, which is suitable for attaching a band to the implant body. The attachment means is preferably an aperture. The aperture is dimensioned so that a band which is suitable for use in attaching the interspinous implant to the spinous processes can pass easily though it. In a preferred embodiment the aperture is at a corner of the implant body and extends between two sides of the implant body. Where two locks are used, the attachment means for each band is at the opposing corner from the hinge of the lock through which that band passes. The attachment means is used to permanently attach a band to the implant body, usually by looping the band through the attachment means and sewing or gluing or otherwise permanently attaching two surfaces of the band together to form a closed loop of the band which is attached to the implant body.

The implant of the present invention can be used with a single band to secure it in place. In this embodiment in use the band passes over one spinous process, is secured to the implant body, usually by passing through an aperture in the implant body, and then passes around the second spinous process and is secured back to the implant body using the hinged lock. In this case the implant will comprise a single hinged lock on one side and a simple means of securing the band to the implant body on the other side, such as an aperture.

However, in a preferred embodiment, the implant is used with two bands, and has two attachment means which are usually diagonally opposed to one another at the corners of the implants to which the locks are hinged. In this embodiment the implant has two locks which are hinged to opposing sides of the implant body from one another. This is advantageous as it is simple to use and provides a very safe and secure way of installing the implant.

It is preferred that the implant body also comprises an aperture to receive the free end of a band. This is positioned on the opposite side of the recess from the attachment means, so that when a band is attached to the attachment means, and the free end of the band passed around the spinous process which sits in the recess, the free end of the band returns to the implant body in the region of the aperture. This is advantageous as it means that once the band is in place and the lock is in the closed position, the band passing through the aperture in the implant body keeps the lock firmly closed and means it is difficult to unintentionally loosen the band or open the lock. The ensures that implant stays safely secured in place.

The implant body and/or the locks of the interspinous implant preferably comprise a material that has similar strength properties to cortical bone, so as to be able to restrict the relative movement of the adjacent vertebrae without damaging the vertebrae. A preferred material is a medical grade polymeric material such as a poly ether ether ketene, commonly referred to as PEEK.

It is particularly preferred that the implant body and/or the locks comprise a radio-opaque material, preferably a material comprising barium sulphate. The barium sulphate can be present at a level of between 5 and 10% by weight. The most preferred material is PEEK comprising 5-10% by weight barium sulphate. It is advantageous to use a radio-opaque material since this shows up on X-rays and so enables a surgeon or clinician to visualise the implant and ensure that it is placed at the correct level.

The implant body of the interspinous implant of the present invention can have an inclined surface forming the side of the implant body or forming a surface of a cavity in the side of the body to which one or each lock is hinged, wherein the inclined surface is inclined towards the hinge. The inclined surface is typically inclined at an angle of between 5 and 60°, generally 5 to 45°. This is advantageous as it acts to guide the band towards the aperture in the lock when it is being fed along the side and therefore makes the implant easier to install.

The interspinous implant according to the first aspect of the present invention is preferably used with a tightening system according to the fifth aspect of the present invention, but can be used with any other tightening system including known tightening systems such as those currently used with the Wallis® implant. Accordingly the implant can comprise a threaded cavity on the upper face of the implant body for engagement with a tightening system, preferably wherein the threaded cavity is substantially in the middle of the upper face. The interspinous implant can also comprise two or more additional cavities on the upper face of the implant body for engagement with a tightening system to ensure stability.

As described above, one or two bands are used to secure the implant of the invention in place in a patient. In particular the band is attached at one end to the implant body, while the free end is passed around one spinous process if using two bands, or both spinous processes if using one band and then secured back to the implant body using the lock. In a preferred embodiment the implant is provided with a band attached to the attachment means of the implant body, and even more preferably the implant body comprises two attachment means diagonally opposed to one another with a band attached to each attachment means.

Suitable bands are known to the person skilled in the art from existing interspinous implants. The band is normally made from a woven synthetic material, preferably woven polyester.

According to a preferred embodiment of the present invention the or each band is heat-treated on at least two strips across the or each band. The heat-treated strips are usually positioned towards the free end of the band so that, in use, when the band has been passed around the spinous process, through the lock and has been tightened, the heat-treated strips will be on the extra unused free end of band that extends from the implant. This is the region in which the surgeon normally cuts the bands at the end of the installation procedure, to ensure that there is not an excess of band left in the body. In the region of the heat-treated strips the fibres of the band will have been melted together so are far less likely to fray than in regions which have not been heat-treated. In use in this embodiment the surgeon cuts the bands on or close to a heat-treated band which will mean that the band will not fray beyond the heat-treated strip. This ensures that the band which is in the lock securing the implant in place cannot fray, which is an advantageous safety feature. This also means that, should the procedure need to be reversed, there will be minimal fraying so it will be easier to remove the band than if more fraying had taken place.

In a further preferred embodiment, the or each band is stiffened at the free end. When the band is stiffened at the end it can more easily be manipulated through apertures such as the aperture in the lock, which makes the procedure easier and less time consuming to perform. The band is normally stiffened by means of the weave, for example by weaving the fibres more densely together in that region than in the main length of the band. Alternatively the band can be stiffened by heat-treatment. In a further embodiment, the or each band is attached to a needle at the free end. This helps the surgeon to pass the band through the tissue around the spinous process, and so can help to make the procedure quicker and easier.

In addition to the implant body, the interspinous implant of the present invention comprises a lock which is hinged to a side of the implant body that does not have the first or second recess. The lock is typically made from the same material as the implant body and is attached securely by hinging the lock to the implant body during the manufacture. The lock can be hinged to the implant body in any way which allows for the relative rotational movement, such as by using a separate hinge element which is attached to both the implant body and the lock. It is, however, preferred that the lock has abutments which fit into cavities in the implant body during manufacture of the implant so that the lock can rotate about the abutments relative to the implant body. The abutments and cavities form the hinge in this embodiment.

The lock can rotate about the hinge between a closed position in which the lock lies substantially within a cavity in the side of the implant body or against the side of the implant body and an open position in which the lock projects away from the side of the implant body. The lock is hinged at or near one end of the lock to allow this movement. When the lock is in the closed position it is preferred that it lies in a cavity in the side of the implant body. This makes the implant a very neat design with no elements extending beyond the outline of the implant body, when the locks are closed. The lock can swing out away from the implant body from the free (i.e. unhinged) end to enable it to project away from the side of the implant body in the open position.

In a preferred embodiment the lock can have a lip on the end which is distal from the hinge. This lip can fit snugly against or snap into place against the aperture in the body to ensure that once the lock has been moved to the closed position, it stays closed.

The lock has an aperture, so that a band can be passed through the aperture in the lock when the lock is in the open position and the band can be secured against movement relative to the lock and the implant body when the lock is in the closed position. The aperture is generally designed to be slightly larger than the band that is used in the procedure, so that the band can pass easily through it. The aperture extends in the direction perpendicular to the length of the side of the implant body. The aperture is often at an angle to aid passage of the band through it and so that the band is forced back on itself when it is tightened. In this embodiment the aperture is angled back towards the hinge from external to internal edge. This helps to ensure that the band is secured against future movement.

In a preferred embodiment, the lock has an upper panel which is positioned adjacent to the upper face of the implant body and a lower panel which is positioned adjacent to the lower face of the implant body, when the lock is in the closed position. The hinging abutments protrude outwards from one end of the upper and lower panels. The aperture is formed by leaving a slot-shaped space in a central region between the upper and lower panels. There is preferably also a space between the upper and lower panels at the end of the lock which is hinged to the implant body, so that the band can pass through this space. In use once the band has encircled the spinous process, the band is typically passed along the side of the implant, through the space at the hinging end of the lock to the external face of the lock, and back through the aperture to contact with the section of band sitting along the side of the implant.

The present invention also relates to a method of making an interspinous implant according to the first aspect of the invention. The method comprises the steps of making the body of the implant, making the lock of the implant, and hinging the lock to the side of the body of the implant, so that it can rotate between a closed position in which it lies substantially within or against the side of the implant body, and an open position in which the lock projects away from the implant body.

Typically the implant body and lock are made separately and then the lock is hinged to the implant body during the manufacturing process. The lock is hinged to the implant body so that it cannot subsequently be removed under normal conditions of use. Removal of the lock from the implant body would require a lot of force and is likely to damage, if not break, the implant, rending it unsuitable for use.

The present invention relates in a sixth aspect to a tightening system which is suitable for use with an interspinous implant, such as the interspinous implant according to the first aspect of the invention. The tightening system of the present invention can also be used with other interspinous implants, such as existing implants. The tightening guide of the tightening system comprises a plate at its distal end and a handle at its proximal end, and brings significant advantages over prior art systems.

First, the plate is suitable for engagement with the body of an interspinous implant to prevent relative rotational movement between the tightening guide and the body. This helps to ensure that any rotational forces applied during tightening are grounded firmly into the implant and are not liable to rotate the implant itself. Second, the plate provides an arcuate tightening surface which contacts the rod during tightening. This helps to locate the rod in the most effective location relative to the implant for tightening and also helps to ensure that all rotational forces are ground into the implant rather than cause the implant to rotate.

The tightening system of the present invention comprises three elements, the holder, the tightening guide and the rod. The holder has engagement means at its distal end which is suitable for engagement with a cavity in the upper face of an interspinous implant. The engagement means is normally a screw thread which engages with a threaded cavity on the upper face of the implant. The holder is typically cylindrical in shape and is made from plastic or metal.

The tightening guide has a hollow section which can be placed over the holder, preferably so that it provides a snug fit. The tightening guide has at its distal end a plate which is suitable for engagement with the body of an interspinous implant to prevent relative rotational movement between the tightening guide and the body. The plate can have protrusions or cavities on its distal surface, which are capable of mating with corresponding cavities or protrusions on the upper face of an interspinous implant. Alternatively, or in addition, the plate of the tightening guide may have flanges that fit around the sides of an interspinous implant. This is particularly preferred as it ensures that that the locks are closed during tightening. This is especially pertinent for prior art implants in which the removable fixing members are liable to become detached during tightening.

The plate of the tightening guide also provides an arcuate tightening surface. In use the rod contacts this and is rotated, guided by this surface. This ensures that the rod is located in the correct place for tightening and cannot move laterally. The tightening guide has at its proximal end a handle which has at least one aperture through it. The aperture is of a suitable size that the tightening rod can pass through it.

The tightening system of the present invention also comprises a tightening rod. The tightening rod has at its distal end an aperture extending lengthwise through which a band can pass, and the tightening rod has at its proximal end a handle. In use the tightening rod is placed though the aperture in the handle of the tightening guide and extends to contact the arcuate tightening surface of the plate, so that when a band is passed through the aperture of the tightening rod, the band can be tightened by rotating the tightening rod relative to the tightening guide.

In a preferred embodiment the tightening guide can be locked in place relative to the holder, preferably by means of a retractable element in the tightening guide that fits into a cavity in the holder, such as a retractable ball or plate.

One problem that has existed with previous implant installation techniques is that the surgeon does not know when the band is sufficiently tight. In a preferred embodiment of the tightening system the tightening rod comprises a torque meter which gives an indication of the tension in the band. This is advantageous as it helps the surgeon to determine and apply the optimal level of tightening.

According to the third aspect of the invention, the interspinous implant is fitted in a subject. According to the fourth aspect it is used to treat degenerative disc disease in a subject or the symptoms of degenerative disc disease. These include pain and restricted mobility. The method of treatment comprises the steps of first providing an interspinous implant according to the first aspect of the invention which has a band attached to it. Second, inserting the body of the interspinous implant between the spinous processes of adjacent vertebrae so that the spinous processes are located in the recesses of the implant body. The recesses can be referred to as superior and inferior recesses as they contact superior and inferior spinous processes. Third, passing the free end of the band around a spinous process and through the aperture in the lock when the lock is in an open position, and fourth closing the lock and tightening the band to secure the implant in place relative to the spinous processes. This method is similar to that used with prior art implants and will be familiar to the person skilled in the art. The difference of using the hinged lock is more straightforward and easier to operate than previous methods of installing an implant. The subject is usually a human but the implant could also be used to treat an animal.

For the tightening step, it is preferred that a tightening system according to the sixth aspect of the invention is used. In particular, the holder is engaged with a cavity on the upper face of the implant and the tightening guide is passed over the holder. The plate of the tightening guide is fitted to engage the implant body securely to prevent relative movement between the guide and the implant. The tightening rod is then passed through the aperture in the handle of the tightening guide and contacts the arcuate tightening surface. The band is passed through the aperture in the rod, and the rod is rotated relative to the guide, which can be held still in place by the handle on the guide. Where the rod includes a torque meter, this can be consulted to determine optimal tension in the band.

BRIEF DESCRIPTION OF THE DRAWINGS

Embodiments of the invention will now be described by way of example only with reference to the accompanying drawings, in which.

DETAILED DESCRIPTION OF EMBODIMENTS

Figure 1:
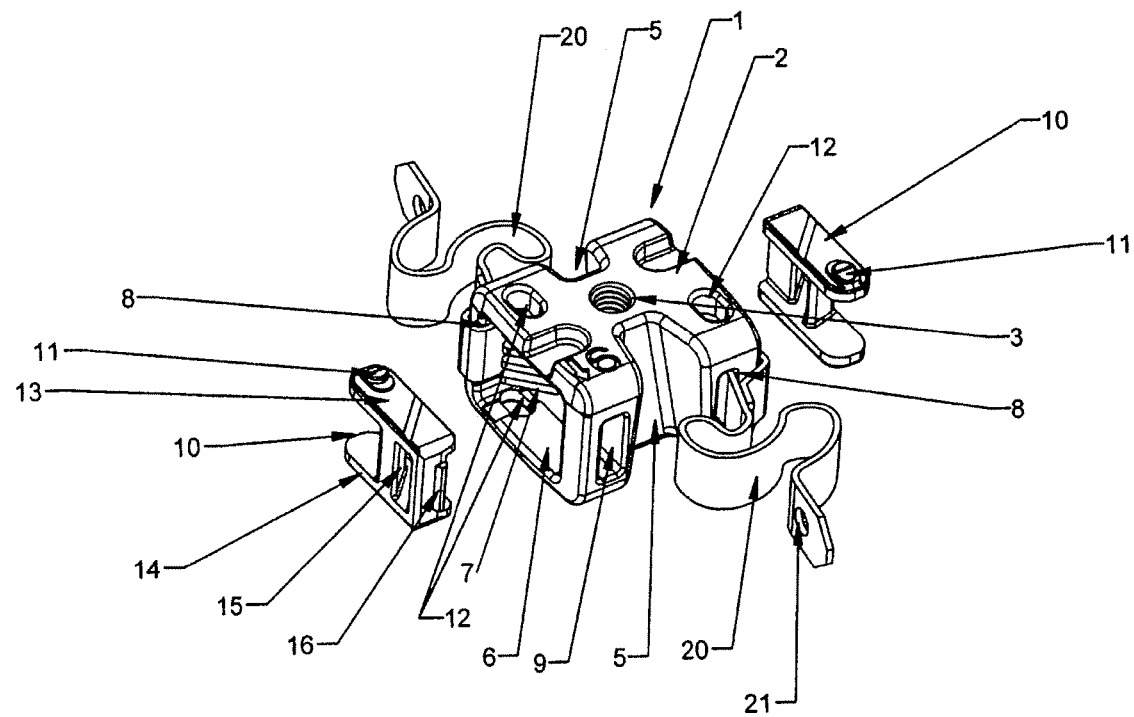
FIG. 1 shows an expanded perspective view of an implant according to a preferred embodiment of the present invention.
Figure 2:
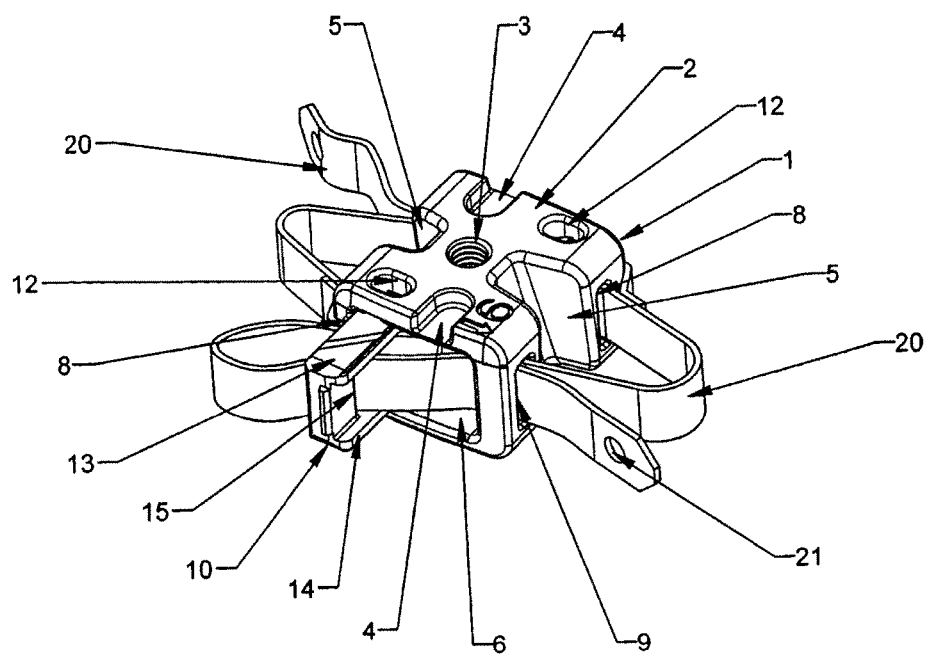
FIG. 2 shows a perspective view of an implant according to a preferred embodiment of the present invention.
Figure 4:
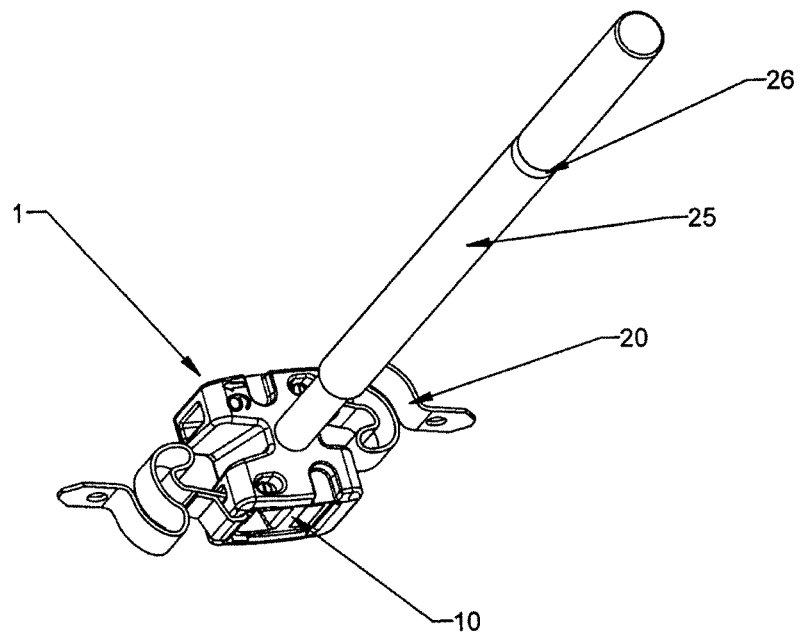
FIG. 4 shows a perspective view of a preferred embodiment of the present invention with a tightening system holder.

FIG. 1 shows an implant according to the present invention which has a implant body 1, two locks 10 and two bands 20. The implant body has an upper face 2 with a central cavity 3 which can be threaded as shown in FIG. 2 for engagement with a tightening system as shown in FIG. 4. The implant body has four sides, two of which have recesses 5 in them which, in use, each receive a spinous process.

Figure 3:
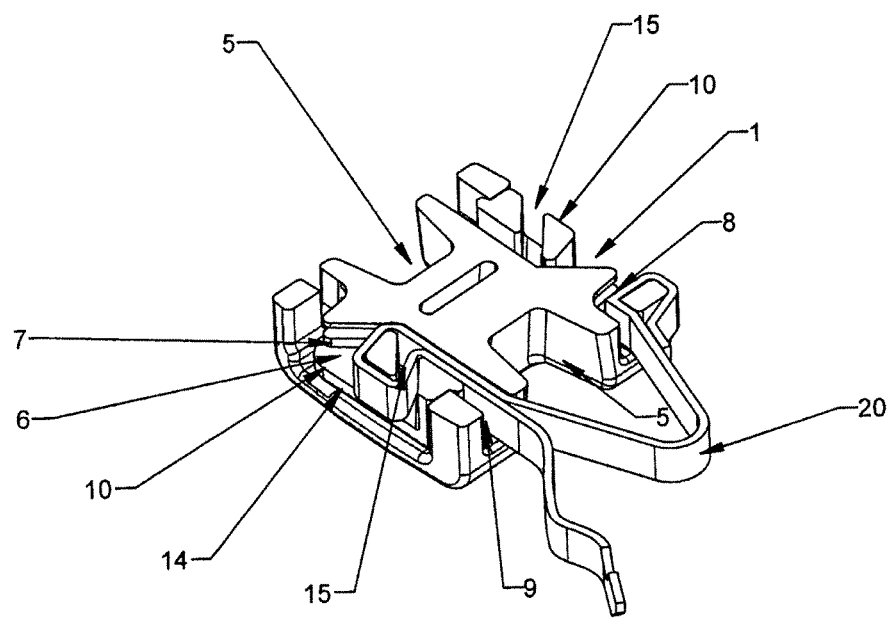
FIG. 3 shows a cross-sectional perspective view of an implant according to a preferred embodiment of the present invention.

The sides of the implant body without the recesses each have a cavities in them 6 with an inclined surface 7. In use the bands are fed up the inclined surface to guide the band to the correct position with respect to the lock 10, as shown in FIGS. 2 and 3.

Each band 20 is attached to the implant body by attachment means which is an aperture 8. The apertures 8 are at opposing corners of the implant body. The implant body also has apertures 9 at the other corners to receive the free end of the band, as shown in FIGS. 2 and 3.

In FIG. 2 the upper face 2 of the implant body 1 has two further cavities 4 that can engage with abutments on the tightening guide.

The locks 10 are hinged to the implant body by means of abutments 11 which are fitted securely during the manufacturing process into holes 12, so that they can not be removed from the implant body under normal conditions without damaging the implant.

The locks have upper and lower panels, 13 and 14 respectively, with a space at the hinged end through which the band can pass during use as shown in FIGS. 2 and 3. The bands also have a aperture 15 through which the free end of the band passes from the external end of the lock back towards the implant. The aperture 15 is angled as shown by the ridge on the top of the lock back towards the hinge from external to internal edge so that the band is forced back on itself when it is tightened. This ensures that the band is secured against future movement.

FIG. 2 shows one lock 10 in the closed position and one lock 10 in the open position, and the location of the band as it is being threaded through the implant body and the lock. In FIGS. 1 and 2, the lock 10 has a lip 16 at its distal end, for engagement with the aperture 9 of the body 1 when the lock is in the closed position, so as to ensure that the lock stays closed and does not accidentally move into the open position.

The bands 20 are made from a woven polyester and have a hole 21 at the free end for engagement with surgical instruments that can be used to pull the band through the interspinous ligaments around the spinous process. The other end is attached to the implant body by looping it through the aperture 8 and fixing the two surfaces of band together.

In use, the interspinous space that needs to be stabilised is cleared by the surgeon and the implant body 1 is positioned between two vertebrae with the adjacent spinous processes in the recesses 5 of the implant body. A band 20 is passed around the spinous process and passed through aperture 9 in the implant body. The band 20 is then fed up inclined surface 7 and passes through the space at the hinged end of lock 10 between upper panel 13 and lower panel 14. The lock 10 is in the open position. The band 20 is then fed back through aperture 15 in the lock 10 and back through aperture 9 in the implant body. The free end of the band 20 is then pulled to tighten the band and close the lock. The friction between the two surfaces of band at the side of the implant body and the forces caused by the angled aperture 15 hold the band securely in place and prevent movement relative to the implant body 1 or the lock 10. The band 20 can then be cut. The heat-treated strips (not shown) on the band 20 are in the region which extends from the implant body 1 after tightening and the band 20 is cut distal of one of the strips to prevent fraying of the part of the band 20 that is being used to secure the implant in place.

FIG. 4 shows an interspinous implant with implant body 1, lock 10 and band 20 which has a holder 25 from a tightening system according to a preferred embodiment of the invention engaged with it. The holder has a screw thread at its distal end (not shown) that is engaged with a threaded cavity on the upper face of the implant body. The holder 25 has a cavity 26 to which the tightening guide can be locked in place by means of a retractable ball (not shown).

Figure 5:
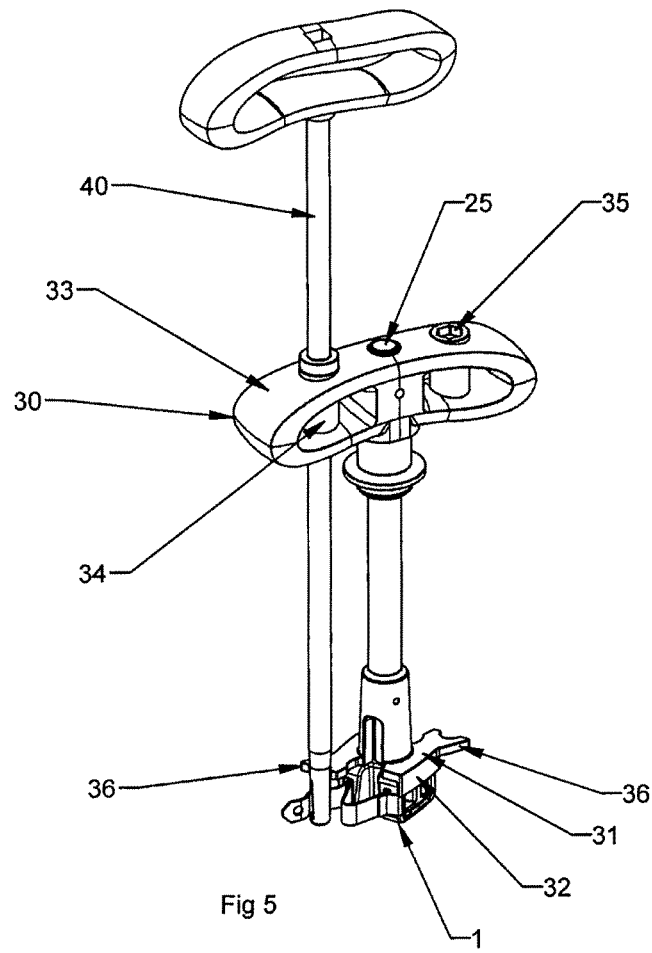
FIG. 5 shows a perspective view of a tightening system according to a preferred embodiment of the present invention engaged with an implant.

In FIG. 5 a tightening guide 30 has been placed over the holder. The tightening guide has at its distal end a plate 31 which has protrusions (not shown) that engage with cavities on the upper face of the implant body (shown as 4 in FIG. 2). The plate 31 also has flanges 32 that extend over the sides of the implant. These flanges improve the engagement of the plate with the implant and prevent the locks 10 from opening during tightening. The plate has arcuate tightening surfaces 36 against which the tightening rod 40 moves during tightening.

Figure 6:
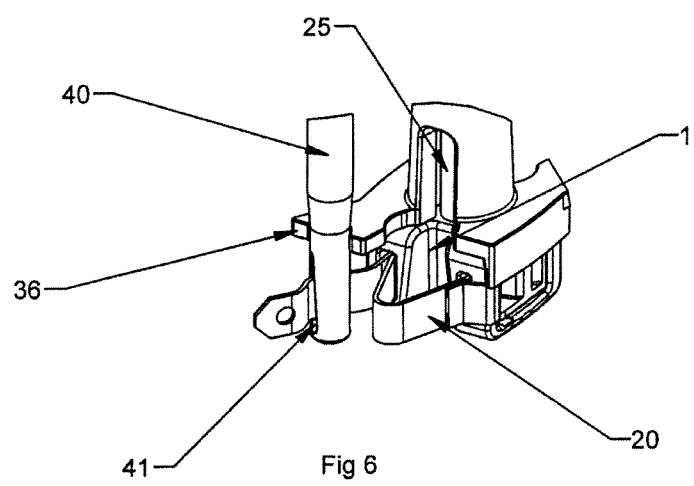
FIG. 6 shows a perspective view of part of the tightening system of FIG. 5.

Tightening guide 30 has at its proximal end a handle 33 that has apertures 34 and 35 through it. Tightening rod 40 passes through aperture 34 and extends down to contact arcuate tightening surface 36. The tightening rod 40 has an aperture 41 in it, which can most clearly be seen in enlargement in FIG. 6. During use, the band 20 passes through the aperture 41 and the rod is rotated to tighten the band.

Although the invention has been described above with reference to one or more preferred embodiments, it will be appreciated that various changes or modifications may be made without departing from the scope of the invention as defined in the appended claims.

The invention claimed is:

1. An interspinous implant comprising:
   (i) an implant body which has an upper face, a lower face, and four sides, wherein the implant body comprises;
      a first recess in one side of the implant body, and a second recess in the opposing side of the implant body to the first recess, wherein each recess is suitable for receiving a spinous process of a vertebrae;
      an attachment means adapted to attach a band to the implant body wherein the attachment means comprises a first aperture which is at a corner of the implant body and which extends between two sides of the implant body; and
      a second aperture, which is enclosed and adapted to receive a free end of a band, extending from the side containing the first or second recess into a cavity in a side of the implant body that does not have the first or second recess; and
   (ii) a lock which is hinged via a hinge to the side of the implant body that does not have the first or second recess;
      wherein the lock can rotate about the hinge between a closed position in which the lock lies substantially within the cavity in the side of the implant body or against the side of the implant body and an open position in which the lock projects away from the side of the implant body;
      wherein the lock has a third aperture, so that a band can be passed through the third aperture in the lock when the lock is in the open position and the band can be secured against movement relative to the lock and the implant body by the lock when the lock is in the closed position.

2. The interspinous implant according to claim 1, wherein the implant comprises two locks which are hinged to opposing sides of the implant body.

3. The interspinous implant according to claim 1, wherein the interspinous implant additionally comprises a band attached to the attachment means of the implant body, wherein the implant body comprises two attachment means diagonally opposed to one another with a band attached to each attachment means.

4. The interspinous implant according to claim 3, wherein each band is stiffened at a free end and/or is attached to a needle at the free end.

5. The interspinous implant according to claim 3, wherein the or each band is made from a woven synthetic material, wherein the or each band is heat-treated on at least two strips across the or each band.

6. The interspinous implant according to claim 1, wherein the implant body and/or the locks comprise a radio-opaque material.

7. The interspinous implant according to claim 1, wherein the implant body has an inclined surface forming the side of the implant body or forming a surface of the cavity in the side of the body to which one or each lock is hinged, wherein the inclined surface is inclined towards the hinge.

8. The interspinous implant according to claim 1, wherein the implant comprises a threaded cavity on the upper face of the implant body for engagement with a tightening system, wherein the threaded cavity is substantially in the middle of the upper face.

9. The interspinous implant according to claim 8, wherein the implant comprises two or more additional cavities on the upper face of the implant body for engagement with a tightening system.

10. A method of making an interspinous implant according to claim 1, the method comprising the steps of:
   making the implant body;
   making the lock of the implant; and
   hinging the lock to the side of the implant body, so that it can rotate between a closed position in which the lock lies substantially within the cavity in the side of the implant body or against the side of the implant body, and an open position in which the lock projects away from the implant body.

11. A method of fitting an implant in a subject, the method comprising the steps of:
- providing an interspinous implant according to claim 1 and which has a band attached to it;
- inserting the implant body of the interspinous implant between the spinous processes of adjacent vertebrae so that the spinous processes are located in the recesses of the implant body;
- passing the free end of the band around a spinous process and through the aperture in the lock when the lock is in an open position; and
- closing the lock and tightening the band to secure the implant in place relative to the spinous processes.

12. A kit comprising the interspinous implant according to claim 1 and further including a tightening system including:
(i) a holder with engagement means at its distal end which is suitable for engagement with a cavity in an upper face of the interspinous implant;
(ii) a tightening guide which can be placed over the holder wherein the tightening guide has at its distal end a plate which is suitable for engagement with the implant body of the interspinous implant to prevent relative rotational movement between the tightening guide and the body, wherein the plate provides an arcuate tightening surface, and wherein the tightening guide has at its proximal end a handle which had at least one aperture through it; and
(iii) a tightening rod, wherein the tightening rod has at its distal end an aperture extending lengthwise through which a band can pass, and the tightening rod has at its proximal end a handle, wherein the tightening rod can be placed though the aperture in the handle of the tightening guide and extends to contact the arcuate tightening surface of the plate of the tightening guide, so that when a band is passed through the aperture of the tightening rod, the band can be tightened by rotating the tightening rod relative to the tightening guide.

* * * * *